US00PP36387P3

(12) United States Plant Patent
Shipley

(10) Patent No.: US PP36,387 P3
(45) Date of Patent: Jan. 14, 2025

(54) ***CALLIANDRA* HYBRID SHRUB NAMED 'MEXICALI ROSE'**

(50) Latin Name: ***Calliandra eriophylla* X *californica***
Varietal Denomination: Mexicali Rose

(71) Applicant: Nicholas Shipley, Tucson, AZ (US)

(72) Inventor: Nicholas Shipley, Tucson, AZ (US)

( * ) Notice: Subject to any disclaimer, the term of this patent is extended or adjusted under 35 U.S.C. 154(b) by 485 days.

(21) Appl. No.: 17/803,805

(22) Filed: Nov. 30, 2022

(65) Prior Publication Data

US 2024/0180052 P1 May 30, 2024

(51) Int. Cl.
*A01H 5/02* (2018.01)
*A01H 6/54* (2018.01)

(52) U.S. Cl.
USPC ..... Plt./226

(58) Field of Classification Search
USPC ..... Plt./226
CPC ..... A01H 5/02; A01H 5/00; A01H 6/54
See application file for complete search history.

(56) References Cited

U.S. PATENT DOCUMENTS

PP15,387 P2 * 11/2004 Gass ..... A01H 5/02
Plt./226

* cited by examiner

*Primary Examiner* — June Hwu

(57) ABSTRACT

A new and distinct hybrid *Calliandra eriophylla* X *californica* named 'Mexicali Rose' shrub is characterized by strong cold hardiness (USDA zone 8), dense, rounded growth form of moderate size (4×5 feet mature), good growth under nursery conditions and a distinctive red flower color (50A).

4 Drawing Sheets

Latin name: *Calliandra eriophylla* X *californica* 'Mexicali Rose'.

Varietal denomination: 'Mexicali Rose'.

BACKGROUND OF THE INVENTION

The present invention relates to a new and distinct *Calliandra* hybrid cultivar. The cultivar originated as an $F_1$ hybrid from an intentional cross: *Calliandra eriophylla* X *Calliandra californica*, both unnamed proprietary open pollinated breeding lines where *Calliandra eriophylla* was the female parent and *Calliandra californica* was the male parent. One of the offspring of this cross exhibited flowers like *Calliandra californica* and cold hardiness like *Calliandra eriophylla* and is the object of this application.

SUMMARY OF THE INVENTION

Among the features that distinguish the new hybrid *Calliandra* cultivar from all other available and commercial varieties of *Calliandra* known to the inventor are the following combination of characteristics: strong cold hardiness (USDA zone 8), dense, rounded growth form of moderate size (4×6 feet mature), good growth under nursery conditions and a distinctive red flower color (50A).

The asexual propagation procedure is as follows: 4 inch long semihardwood cuttings are prepared by removing the lower leaves, dipping the cut end into a 1:5 mix of DIP'N GRO™, then placing the treated cuttings into trays of peat media. The trays are maintained at a soil temperature of 72° F. and an air temperature of 75-85° F. with mist applied 12 times per hour. Cuttings are rooted in about 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Calliandra eriophylla* X *californica* 'Mexicali Rose' growing in the ground at a commercial nursery near Sahuarita, Ariz. aged 3 years and in a #5 nursery pot aged 1.5 years from a cutting growing near Tucson, Ariz., depicted in color as nearly correct as it is possible to make in a color illustration of the character.

DETAILED PLANT DESCRIPTION

Figure 1:
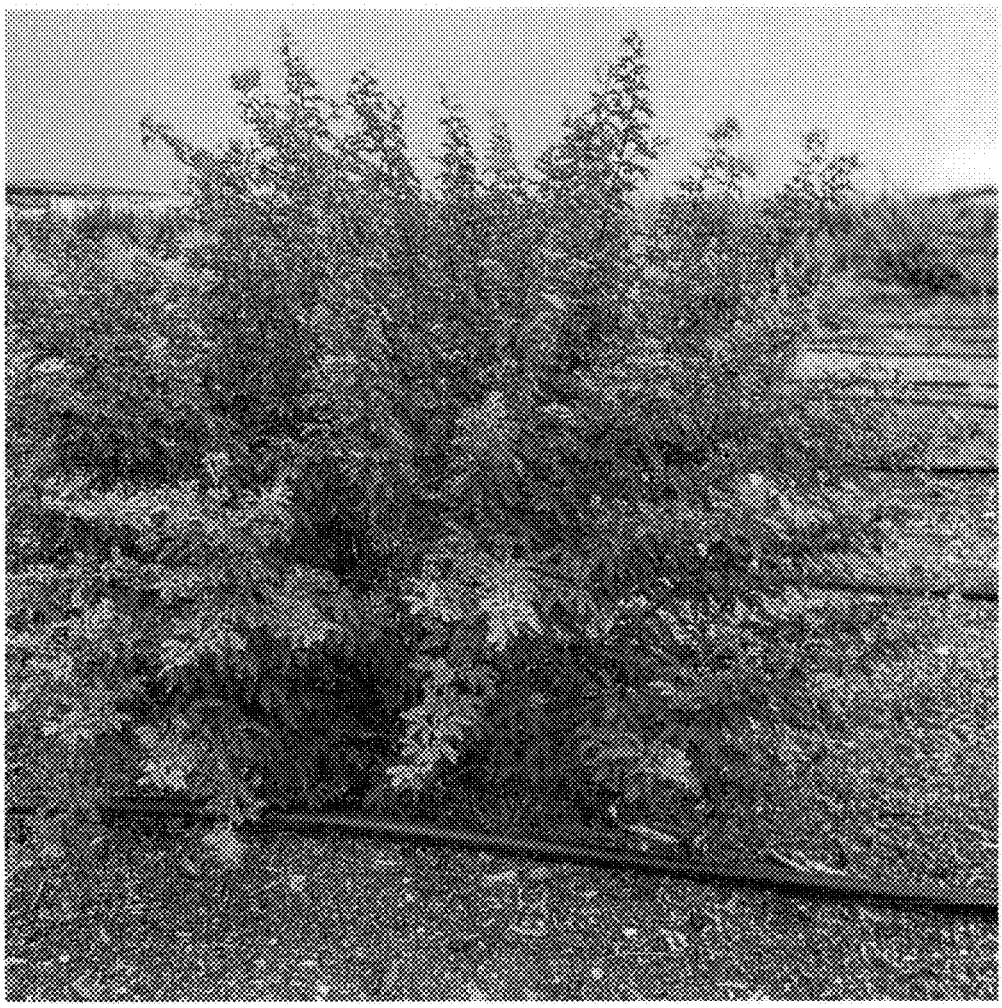
FIG. 1 shows *Calliandra* hybrid 'Mexicali Rose' aged 3 years growing under irrigation at a commercial nursery near Sahuarita, Ariz.
Figure 2:
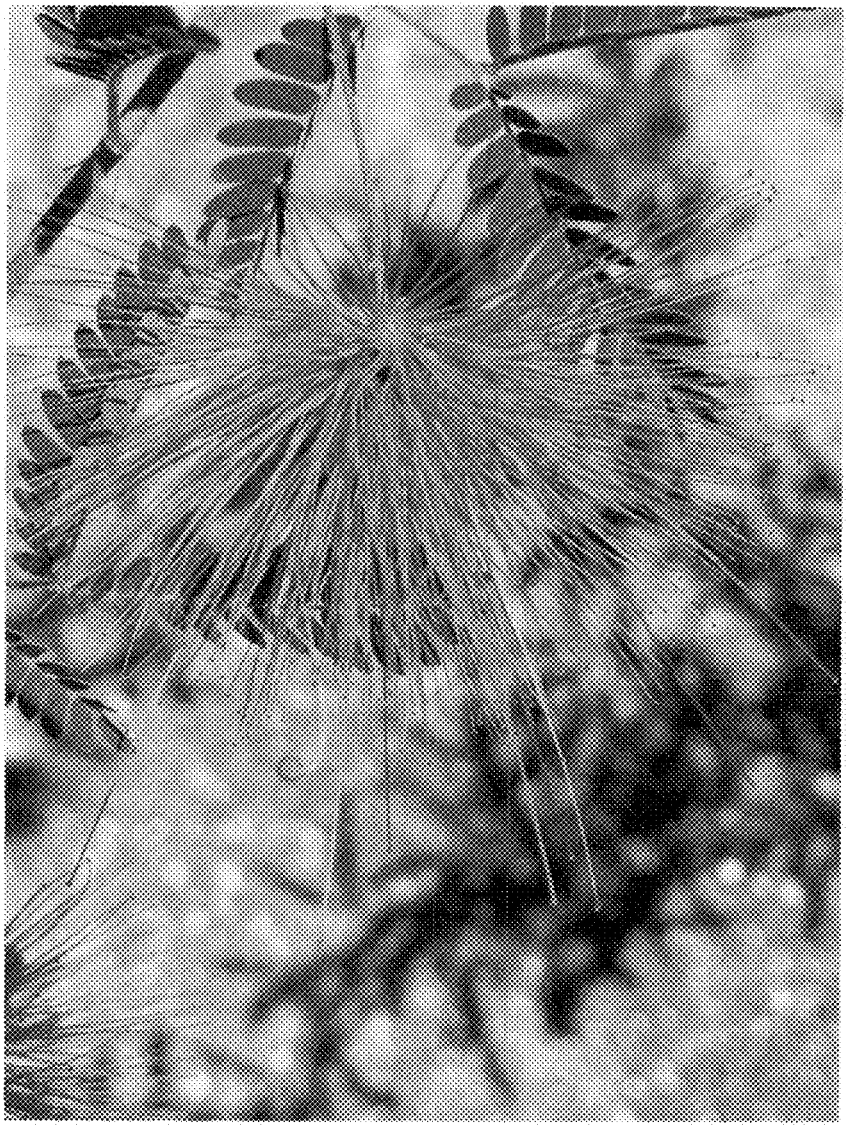
FIG. 2 shows a typical inflorescence of *Calliandra* hybrid 'Mexicali Rose'. Note the uncoiling and extension of the style of a flower near the lower center of the inflorescence.
Figure 3:
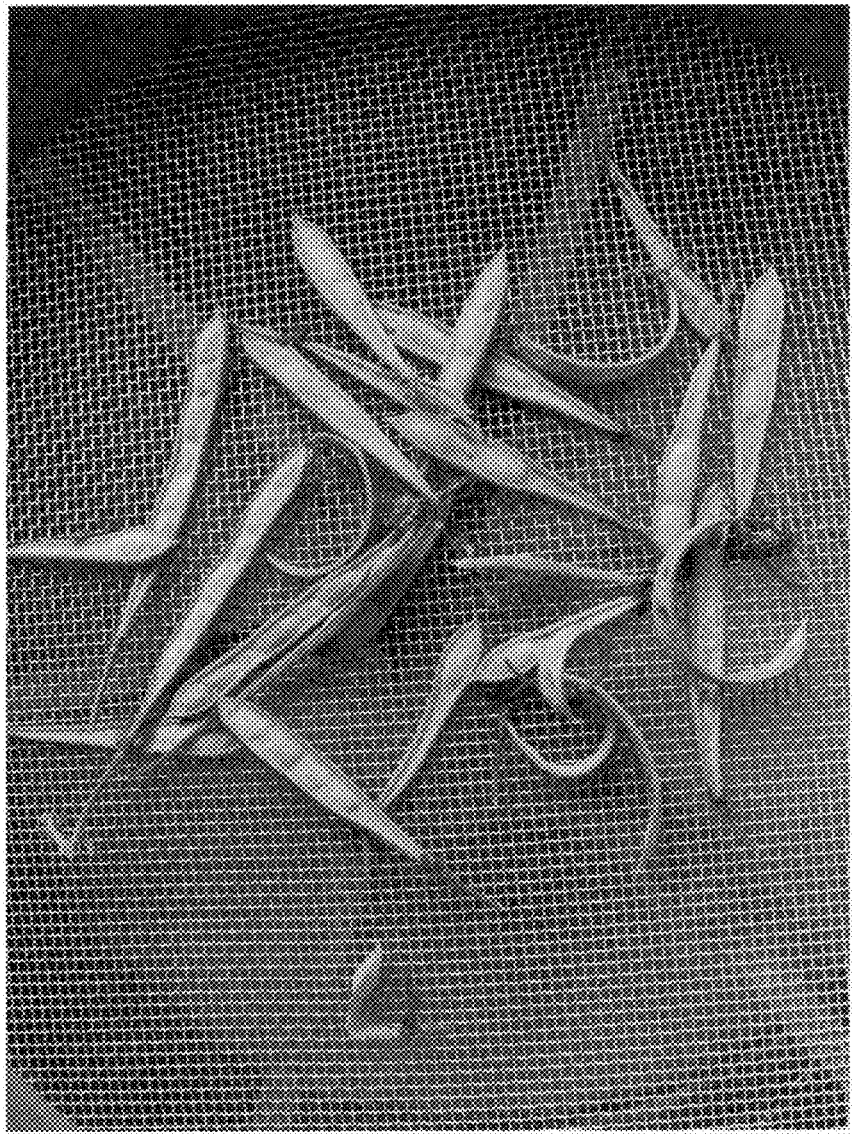
FIG. 3 illustrates mature fruits of *Calliandra* hybrid 'Mexicali Rose'.
Figure 4:
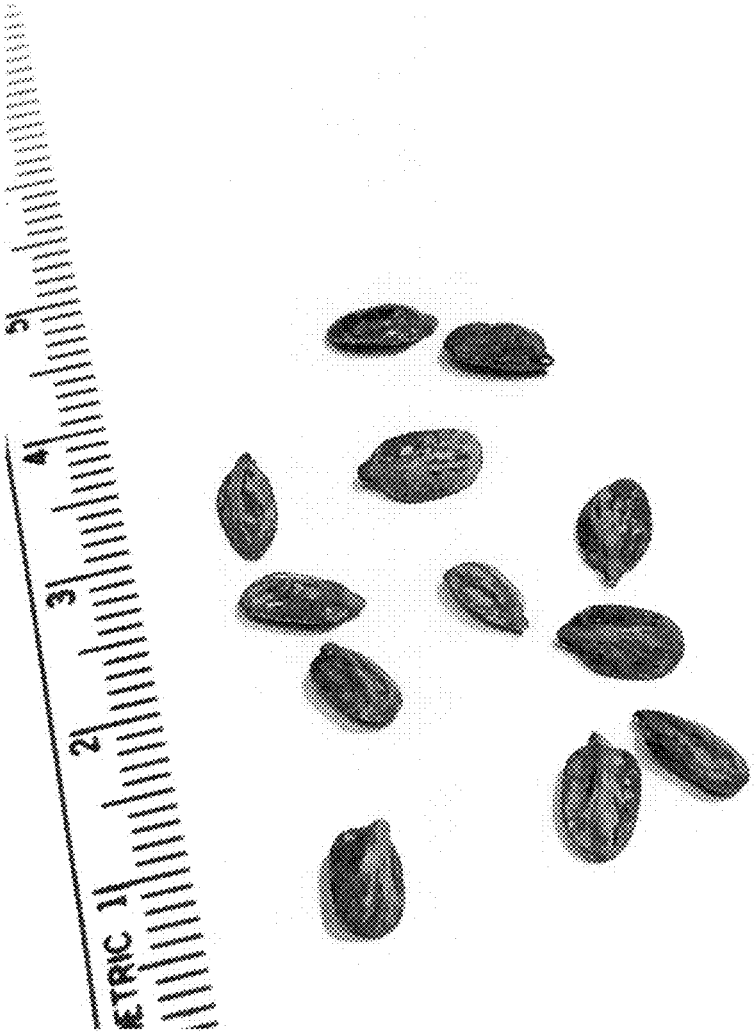
FIG. 4 shows seeds from *Calliandra* hybrid 'Mexicali Rose'.

The following is a detailed description of the new *Calliandra* hybrid plant based upon a plant aged from 1.0 to 1.5 years from cutting growing in a #5 pot near Tucson, Ariz.

The color descriptions are based upon the $5^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant a densely branched shrub, at age 1 year from cutting growing in a #5 nursery pot the plant measures roughly 50 cm tall×50 cm wide. Growing in the ground expected ultimate size is 4 feet tall×5 feet wide. No disease or insect problems have been noted. Actively growing portions of the plant are hardy to 25° F. Portions not in active growth are hardy to 20° F. All branches begin to be damaged at 18° F., USDA hardiness zone 8. Plants recover quickly from freeze damage when warm weather returns in spring.

Stems are stiff and strong. Young stems are puberulent, the hairs caducous soon after stem maturation. Young stems measure 1.5-2.0 mm in diameter, terete, weakly zig zag at the nodes, stem color 177A. Internodes measure from 3.0-36 mm in length. Older stems measure 2-5 mm in diameter and are mostly glabrous and elongated reticulate, with scattered oval lenticels aligned perpendicular to the stem axis, the major axis measuring from 0.5-1.0 mm and the minor axis measuring 0.3-0.5 mm, lenticel color 165B. Older stems are colored 177A. Branch angle varies from 30-60°.

Axillary buds are ovoid, measuring 1.8 mm long×1.0 mm wide, imbricate, glabrous, color 177A. Leaves are alternately arranged. Leaves are even bipinnately compound, overall leaf shape being roughly ovate. Leaves with two pairs of pinnae, each with from 16-22 leaflets. Leaves measure from 24-35 mm long×25-28 mm wide. Stipules 2, triangular and colored like the stems (177A), measuring 3 mm long×1 mm wide, ciliate and caducous soon after leaf maturation.

The leaf petiole measures 5 mm in length and diameter 1.25 mm basally tapering to 1.0 mm at the first pinna. The surface is puberulent, the hairs thinning with age. Petiole color is 138B, the petiole hairs 157D. The leaf rachis measures 6 mm long×0.7 mm in diameter, puberulent color 138B, hairs 157D.

Each leaf pinna has a pulvinus and is subtended by one stipel per pinna pair. These stipels measure 2 mm long×1 mm wide, abaxially puberulent, adaxially glabrous, triangular, caducous, color 138B both surfaces. Pinnae measure 15-26 mm long×4-7 mm wide, folding with water stress and at night. Petiolule measures 2-3 mm in length, of which the pulvinus comprises from ½-⅔ of that length. The pulvinus measures 1.0-1.3 mm in length and 0.5 mm in diameter. The pulvinus is puberulent, colored 194A, the hairs 157D. The remainder of the petiolule is puberulent and colored 138B, the hairs 157D.

Leaflets measure 3.5-5.0 mm long×1.6-2.0 mm wide, oblong in shape, sparsely pubescent on both surfaces with appressed hairs. Leaflet base is oblique, the apex obtuse and apiculate. The abaxial surface is colored 146B, the adaxial surface 146A, the hairs on both surfaces colored 157D.

Inflorescence is axillary, comprised of umbel like heads made up of 7-11 flowers each. The flowers of the inflorescence spread at an angle of about 160°. The peduncle is terete, 23-27 mm in length and slightly tapering in diameter from 0.8 mm at the base to 0.7 mm just below the inflorescence. The peduncle is puberulent with ascending, somewhat erratic hairs which are densest at the basal 1 mm and gradually decreasing in density apically. The hairs are colored 155C. The sunward side of the peduncle is colored 187A and the shaded side is colored 148B, the colors transitioning gradually at the sun/shade margins. A bract is present at ⅔ the length of the peduncle above the base. This bract is ciliate, spotted with round glands measuring 30 μ in diameter colored 187A. The bract measures 1.5 mm long× 0.5 mm wide, lanceolate in shape, color 148B. These bracts are appressed to slightly flaring apically.

Inflorescences usually last about a week, with individual flowers remaining fresh for about 3 days. Mature buds are obovoid in shape, measuring 6 mm long×3 mm wide, sparsely pubescent, the hairs appressed, all colored 59C.

Flowers are perfect, the long stamens spreading at an angle of 30°. Flowers are without a notable fragrance. Flower color which is seen is based upon the color of the staminal filaments and ovary style, which constitute the main visible flower. Individual flowers at anthesis measure 32 mm long×23 mm wide at the anthers, 3 mm wide at the floral tube. One floral bract located just below the calyx is ciliate and ovate in shape measuring 1.5 mm long×0.5 mm wide and colored 145D. The ciliate hairs are colored 145D.

Calyx is campanulate, basally fused, measures 2 mm long×2.5 mm wide. Abaxial surface is pubescent with apically appressed hairs colored 145D. Calyx is colored 145D both internally and externally. Adaxial surface is glabrous. Triangular calyx lobes measure 1.25 mm long and 1 mm wide at the base.

The corolla is comprised of 5 petals fused up to 2.5 mm from the base, then with flaring to retrorse lobes. The corolla overall is trumpet shaped. The abaxial corolla surface is pubescent with apically appressed hairs colored 50D. The corolla adaxial surface is glabrous and colored like the abaxial side. The tube portion of the corolla is colored 50D which gradually transitions to 50A at the fusion point of the petals. The corolla lobes are colored 50A. The corolla measures overall 4 mm long×8 mm in diameter. Corolla lobes are ovate and measure 3 mm long×2 mm wide.

The androecium is comprised of about 25 stamens which are fused up to 2 mm above the receptacle, then free and separate. The fused portion is glabrous and colored 36A. Total stamen length is 29 mm. The color of the staminal filaments changes abruptly to 50A above the fused portion. Filaments are 26.5 mm long, terete and measure 0.2 mm in diameter. The filaments are covered with scattered sparkling glitter like spots measuring 10 μ in diameter and colored 30C but are brighter (more luminous) than the color sample. Anthers are dorsifixed, flying saucer shaped and terminal perpendicular to the axis of the filament. Anthers measure 0.4 mm long×0.2 mm wide and are colored 59B. Pollen is spherical, measuring about 30μ in diameter, colored 8D.

The pistil measures 3.25 mm long at anthesis. The ovary consists of one carpel and measures 1 mm long and 0.3 mm wide. The ovary is colored 153B basally gradually transitioning to 79B at the ovary apex. The style measures 2 mm long and 0.15 mm in diameter and is tightly coiled apically. The style color at this stage of development is 164D. The coil measures 0.7 mm in diameter. Apparently, the pistil development lags that of the stamens and the style unrolls and extends in length to 42-45 mm and the color transitions as well becoming like that of the stamens some time after anthesis (50A). The stigma at anthesis is rounded, 0.4 mm in diameter, colored 165A.

Fruit is an explosively dehiscent legume. The ovary contains up to 9 or more ovules, but usually only 1-3 of these produce mature seeds. Exceptionally under ideal conditions the inventor has seen up to 7-9 seeds in a single fruit. Dry mature fruits measure 35-95 mm long×6.5-7.0 mm wide at the widest point, color 166C. The fruit margin is strongly rimmed (color 166B). Fruits are externally finely puberulent (less densely so on the rims) and are roughly oblanceolate in shape. The fruit hairs are colored NN155B. Fruit is internally glabrous, irregularly colored from 164B to 164C to 164D.

Seeds appear to be tick mimics, possibly to attract birds to aid in seed dispersal. They are roughly a flattened ovoid in shape, measuring 6.0-7.5 mm long×3.5-4.0 mm wide× 2.0-2.5 mm thick. The hilum sits atop a roughly conical projection from the seed (the tick's head) which is about 1 mm tall×1 mm wide at the seed end. Seeds have a rounded ridge running down both flattened sides of the seed that measures from 1.5-2.0 mm wide and raised from 0.5-0.75 mm above the general surface of the seed's sides. The seed color pattern is a base color of 165C heavily mottled with rounded spots colored 203D and varying from 20-300 μ in diameter, but predominantly close to 30 μ. The base color is mostly unspotted in a pattern radiating fanlike away from the hilum as well as a few scattered unspotted irregular blotches measuring 0.5-1.5 mm in size.

COMPARISONS TO RELATED *CALLIANDRAS*

Compared to *Calliandra eriophylla*, the female parent, 'Mexicali Rose' has red flowers (50A) compared to variably pink flowers in the female parent line. 'Mexicali Rose' has a dense canopy compared to an open branched form in the female parent.

Compared to *Calliandra californica*, the male parent, the flowers of 'Mexicali Rose' are similar in color. The male breeding line has an upright growth form while 'Mexicali Rose' is broader.

'Mexicali Rose' is cold hardy to 20° F. on mature growth while the male parent is badly freeze damaged by temperatures below 25° F.

Compared to *Calliandra* hybrid 'Lianca' U.S. Plant Pat. No. 15,387, 'Mexicali Rose' has a different flower color (50A compared to 53C). 'Lianca' begins to become deciduous at about 30° F. while 'Mexicali Rose' holds its leaves to 25° F. Ultimate survival cold hardiness appears to be similar for both cultivars. The ultimate plant size of 'Mexicali Rose' is smaller than 'Lianca' at 4 feet tall compared to 5 feet tall.

Compared to unpatented *Calliandra* hybrid 'Maricopa Red', 'Mexicali Rose' is considerably smaller at 4 feet tall compared to 6+ feet tall for 'Maricopa Red'. 'Mexicali Rose' has a dense growth habit compared to the open growth habit of 'Maricopa Red'.

Compared to *Calliandra californica* 'Cascada Desiertica' U.S. Plant Pat. No. 20,039, 'Mexicali Rose' has a rounded, dense growth form while 'Cascada Desiertica' is strongly prostrate. Flower color (stamen filaments) is reported as 45B, 45C, 45D while those of 'Mexicali Rose' are colored 50A.

I claim:

1. A new and distinct hybrid *Calliandra eriophylla* X *californica* shrub named 'Mexicali Rose' substantially as described and illustrated herein.

* * * * *